(12) United States Patent
Bertsch

(10) Patent No.: US 7,722,545 B2
(45) Date of Patent: May 25, 2010

(54) SURFACE STRUCTURE FOR A CATHETER SLIDING SURFACE

(75) Inventor: Torben Bertsch, Nuremberg (DE)

(73) Assignee: Biotronik Mess- und Therapiegeraete GmbH & Co. (DE)

( * ) Notice: Subject to any disclaimer, the term of this patent is extended or adjusted under 35 U.S.C. 154(b) by 1461 days.

(21) Appl. No.: 10/391,504

(22) Filed: Mar. 18, 2003

(65) Prior Publication Data

US 2004/0106930 A1 Jun. 3, 2004

(30) Foreign Application Priority Data

Mar. 21, 2002 (DE) ................... 102 13 368

(51) Int. Cl.
*A61B 5/02* (2006.01)
(52) U.S. Cl. ...................................... 600/504
(58) Field of Classification Search ............ 600/504, 600/585, 434, 435; 604/282, 280, 523; 606/200, 606/108
See application file for complete search history.

(56) References Cited

U.S. PATENT DOCUMENTS

| | | | | |
|---|---|---|---|---|
| 5,180,364 A | * | 1/1993 | Ginsburg | .................. 604/510 |
| 5,423,774 A | | 6/1995 | Fischell | |
| 5,681,296 A | * | 10/1997 | Ishida | .................. 604/523 |
| 5,779,670 A | | 7/1998 | Bidwell et al. | |
| 6,537,480 B1 | * | 3/2003 | Becker et al. | .............. 264/400 |

FOREIGN PATENT DOCUMENTS

| | | |
|---|---|---|
| DE | 3045237 A1 | 7/1982 |
| DE | 3441586 A1 | 5/1986 |
| DE | 41 41 787 A | 7/1993 |
| DE | 0 795 339 A1 | 9/1997 |
| DE | 196 09 714 A | 9/1997 |
| EP | 0 384 476 A1 | 8/1990 |
| EP | 1 082 974 A | 3/2001 |
| JP | 11028184 A | 7/1997 |
| WO | WO 96/01662 A | 1/1996 |
| WO | WO 99/36490 A | 7/1999 |
| WO | WO 99/49790 A | 10/1999 |
| WO | WO 01/43807 A | 6/2001 |

* cited by examiner

*Primary Examiner*—Max Hindenburg
*Assistant Examiner*—Fangemonique Smith
(74) *Attorney, Agent, or Firm*—Hahn Loeser & Parks, LLP; John J. Cunniff

(57) ABSTRACT

The invention consists of a surface structure for a friction or sliding surface of a catheter (10) or guide wire (12) characterized by a plurality of recesses (18) distributed on the surface for accommodating a friction-reducing fluid and by sliding surfaces (20) between the recesses (18).

15 Claims, 1 Drawing Sheet

SURFACE STRUCTURE FOR A CATHETER SLIDING SURFACE

The invention concerns a surface structure for a friction or sliding surface of a catheter or guide wire.

BACKGROUND OF THE ART

Catheters or guide wires are basically known medical implements which are designed in various forms for insertion into body cavities such as for example blood vessels. Catheters of that kind are for example catheters for percutaneous transluminal coronary angioplasty (PTCA) or also electrode lines for electrostimulation, that is to say for example for intracardial defibrillation. In particular catheters for insertion into blood vessels are frequently of great length and must follow the configuration of the blood vessels in respect of all branchings and windings and therefore have to be flexible. In its implanted condition such a catheter has a larger number of bends over its length.

The catheters which are of interest here are those which have a lumen, that is to say a cavity extending over the length of the catheter, into which for example a guide wire, a mandrin or a stilette or another kind of 'core' can be longitudinally or rotationally movably introduced. Particularly in the case of catheters with a large number of bends the problem which arises is that unwanted frictional losses occur between friction or sliding surfaces of the catheter or the core, that is to say the inside wall of the lumen and for example the outside surface of the core. Those frictional losses can for example adversely affect the precision of the movement of the stilette or guide wire in the catheter. A similar problem arises in relation to surfaces, which are movable relative to each other, of the control wires provided for lateral deflection for example of a guide wire, in the interior of the guide wire.

SUMMARY OF THE INVENTION

The object of the invention is to provide more precise catheters of the above-indicated kind.

In a catheter or guide wire of the kind set forth in the opening part of this specification that object is attained by a surface structure for a sliding or friction surface of said catheter or guide wire, which is distinguished by a plurality of recesses distributed on the surface for accommodating a fluid for contributing to a reduction in friction and by at least one sliding surface between the recesses. That sliding surface delimits the recesses both in the peripheral direction of the catheter or guide wire and also in the longitudinal direction. The recesses are therefore non-interconnected crater-like recesses which are let into a continuous sliding surface.

In a preferred embodiment the ratio of largest to smallest extent of a respective recess on the catheter surface is less than 2. In this respect the term extent of a recess on the catheter surface is used to denote the diameter of the recess in the direction of the catheter surface. In the case of recesses which for example are of a round configuration there is only one diameter so that the ratio of largest to smallest extent is 1. Oval or elliptical recesses can involve a different diameter ratio which however is not to be greater than 2.

The contour of the recesses on the catheter surface is preferably roundish, that is to say for example circular, oval or elliptical.

A suitable fluid for contributing to a reduction in friction is for example a saline solution as it can be adjusted to be physiologically compatible. Other fluid mixtures preferably containing physiologically compatible fluids or for example a saline solution and optionally a contrast agent also fall to be considered.

The surface structure according to the invention can be advantageously used in the broadest sense wherever, in relation to flexible medical implements, friction or sliding movements occur within the contact zones, between or on surfaces on component parts of the medical implement.

Preferably the recesses are distributed uniformly over the friction or sliding surface, wherein the recesses particularly preferably differ from each other in respect of their size. That distribution of the recesses of differing sizes is preferably irregular. Thus the preference is for a distribution of the recesses of different sizes over the friction or sliding surface, which distribution is admittedly uniform but does not follow strict rules and is systematic but for example quasi-random.

Depending on the respective use involved however a regular or systematic distribution of the recesses can also be advantageous.

The transitions between the sliding surfaces between the recesses and the recesses themselves are preferably rounded.

In a preferred embodiment the above-described surface structure is provided on the inside of a lumen of a catheter.

Alternatively the described surface structure is provided for the outside surface, serving as a sliding surface, of a guide wire.

Equally the surface structure can be provided for the sliding surface of a stilette or mandrin. The last-mentioned case does not only have to involve the sliding surface between for example the stilette or mandrin and the inside wall of a lumen of a catheter, but rather the sliding surface with the corresponding surface structure can also be one of the sliding surfaces between the components, which serve for deflection or control, of a stilette, mandrin or guide wire.

BRIEF DESCRIPTION OF THE DRAWINGS

The invention will now be described in greater detail by means of an embodiment with reference to the Figures.

In the Figures.

DETAILED DESCRIPTION OF THE DRAWINGS

Figure 1:
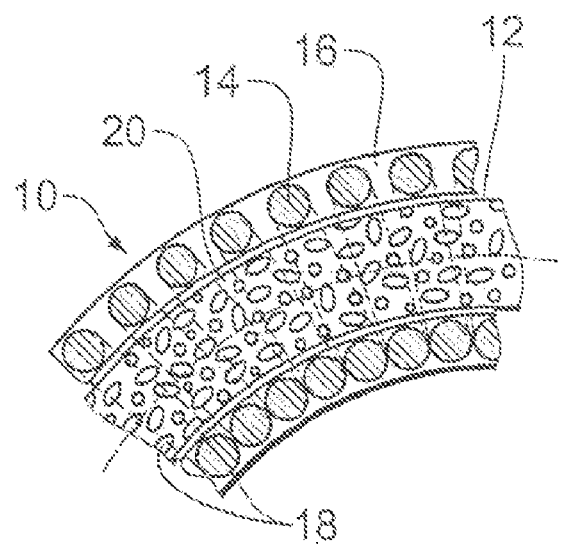
FIG. 1 shows a portion of a catheter with a lumen and a guide wire disposed therein, in partial section.

FIG. 1 shows a portion of a catheter 10 with a portion disposed therein of a guide wire 12. In this case the catheter portion 10 is shown in section while the guide wire 12 is not sectioned.

The catheter portion 10 is formed by a metal helix 14 which is embedded in elastic wall material 16, containing for example silicone. The wall material 16 with the metal helix 14 embedded therein enclose a cavity which forms a lumen for the guide wire 12.

On its outside the guide wire 12 has a surface structure formed by evenly but not regularly distributed recesses 18 of differing sizes. In this case the dimensions of the recesses 18 are so selected that, in the peripheral direction of the guide wire 12, each recess extends only over a fraction of that periphery, for example over less than $1/10$th of the periphery. The fraction crucially depends on the total periphery of the sliding surface and is to have a tendency to be selected to be smaller, with increasing periphery or diameter.

The recesses 18 are preferably of roundish shape, for example circular or elliptical.

A fluid-filled intermediate space is provided between the catheter portion 10 and the guide wire 12. That fluid is distributed over the recesses 18 so that the recesses 18 contain small supplies of the fluid. The fluid reduces the friction between the sliding surfaces 20 of the guide wire 12 and the inside wall of the lumen of the catheter. The sliding surfaces therefore have a function of bearing the fluid film and are to be of corresponding size.

A suitable fluid is physiologically compatible saline solution.

The transition between the recesses 18 and the sliding surfaces 20 between the recesses is rounded.

Figure 2:
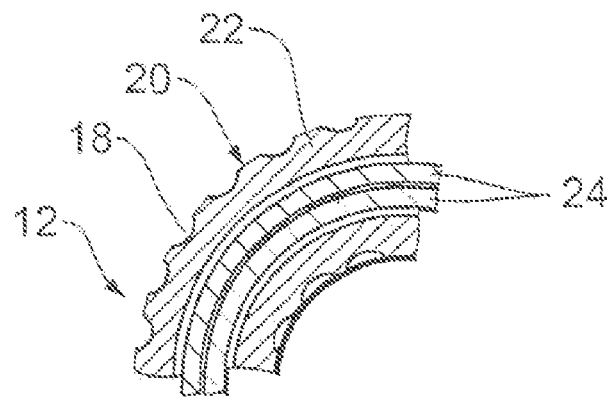
FIG. 2 shows a view in longitudinal section through a portion of a guide wire.

FIG. 2 shows a guide wire 12 similar to that of FIG. 1, but this time in section. It is possible to see therefrom a casing 22 of the guide wire 12, which on its outside surface carries recesses 18 and sliding surfaces 20 disposed therebetween.

The casing 22 also encloses an elongate cavity which accommodates control means 24 formed for example by flat metal strips for the illustrated lateral deflection of the guide wire 12. The control means 24 are adapted to produce lateral deflection of the guide wire 12 by axial relative displacement of the control means with respect to each other. Accordingly there is a sliding surface between the two control means 24. One of the surfaces of the control means 24, which form that sliding surface, can also be provided with a surface structure as described hereinbefore.

Figure 3:
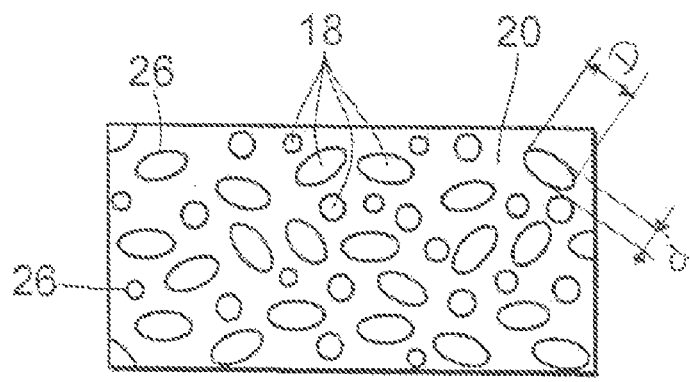
FIG. 3 is a view by way of example of the development of a suitable surface structure.

FIG. 3 shows a suitable surface structure for sliding or friction surfaces of flexible medical implements on an enlarged scale. In particular the Figure shows the admittedly irregular but uniform distribution of the recesses of different sizes. In order to provide a uniform but irregular distribution, the recesses 18 of different sizes can be distributed over the surface in a quasi-random fashion.

It can be seen from FIG. 3 that the recesses 18 are all of circular or elliptical or oval contours 26. In addition the Figure shows in relation to one recess the largest extent D thereof on the catheter surface and the smallest extent d thereof on the catheter surface. The ratio of D/d is preferably not very much greater than 2 and particularly preferably is between 1 and 2.

The catheter 10 shown in FIG. 1 is preferably either an electrode line for a cardiac pacemaker or defibrillator or however also a catheter for intraluminal placement of prostheses such as stents or the like.

I claim:

1. A surface structure for a sliding surface of a catheter or guide wire, said sliding surface having a longitudinal and a peripheral direction, said surface structure comprising:

a plurality of recesses distributed on the surface for accommodating a fluid contributing to a reduction in friction; and at least one continuous sliding surface between the recesses;

wherein the at least one continuous sliding surface delimits the recesses in respect of their dimensions on the catheter surface both in the longitudinal direction and also in the peripheral direction; and wherein said sliding surface is located in a lumen of a catheter.

2. The surface structure of claim 1, wherein: a ratio of the greatest extent of any of said recesses on the sliding surface to the smallest extent of said recess on the sliding surface is less than 2.

3. A surface structure for a sliding surface of a catheter or guide wire, said sliding surface having a longitudinal and a peripheral direction, said surface structure comprising:

a plurality of recesses distributed on the surface for accommodating a fluid contributing to a reduction in friction; and at least one continuous sliding surface between the recesses;

wherein the at least one continuous sliding surface delimits the recesses in respect of their dimensions on the catheter surface both in the longitudinal direction and also in the peripheral direction;

wherein said sliding surface is located in a lumen of a catheter; and the plurality of recesses are uniformly distributed over the sliding surface.

4. The surface structure of claim 1 wherein: the plurality of recesses are irregularly distributed by size over the sliding surface.

5. The surface structure of claim 4, wherein:

a transition between any one of the sliding surfaces and any one of the recesses is rounded.

6. The surface structure of claim 5, wherein:

each of the recesses has a peripheral extent in the peripheral direction of the sliding surface that is less than 1/10th of the periphery of the sliding surface.

7. The surface structure of claim 6, wherein: the recesses are generally of a round shape.

8. A catheter, comprising:

a lumen which has an internal surface with the surface structure of claim 7.

9. A catheter, comprising: a lumen which has an outside surface with the surface structure of claim 7.

10. A guide wire, comprising: an outside surface with the surface structure of claim 7, wherein the guide wire is adapted for insertion into a lumen of a catheter.

11. A stilette, comprising:

an outside surface with the surface structure of claim 7, wherein the stilette is adapted for insertion into a lumen of a catheter.

12. A surface structure for a sliding surface of a catheter or guide wire, said sliding surface having a longitudinal and a peripheral direction, said surface structure comprising:

a plurality of recesses distributed on the surface for accommodating a fluid contributing to a reduction in friction; and at least one continuous sliding surface between the recesses;

wherein the at least one continuous sliding surface delimits the recesses in respect of their dimensions on the catheter surface both in the longitudinal direction and also in the peripheral direction;

wherein said sliding surface is located in a lumen of a catheter; and the plurality of recesses are of different sizes.

13. The surface structure of claim 1, wherein:

a transition between any one of the sliding surfaces and any one of the recesses is rounded.

14. The surface structure of claim 1, wherein:

each of the recesses has a peripheral extent in the peripheral direction of the sliding surface that is less than 1/10th of the periphery of the sliding surface.

15. A mandrin, comprising: an outside surface with the surface structure of claim 7, wherein the mandarin is adapted for insertion into a lumen of a catheter.

* * * * *